United States Patent [19]

Lloyd

[11] Patent Number: 5,181,743
[45] Date of Patent: Jan. 26, 1993

[54] DRUG INFORMATION REQUEST SYSTEM

[76] Inventor: Christopher Lloyd, 8533 Delmeade, Ville de Mount-Royal, Quebec, Canada, H4T 1M1

[21] Appl. No.: 886,848

[22] Filed: May 22, 1992

[51] Int. Cl.⁵ ............................................. G09B 19/22
[52] U.S. Cl. .................................... 283/48.1; 283/56; 283/900; 434/363
[58] Field of Search .................. 283/48.1, 56, 66.1, 283/116, 70, 62, 900; 434/363

[56] References Cited

U.S. PATENT DOCUMENTS

| | | |
|---|---|---|
| 1,363,081 | 12/1920 | Brown . |
| 1,588,964 | 6/1926 | Hutchins .................... 283/48.1 X |
| 3,517,449 | 6/1970 | Frandsen et al. . |
| 4,460,824 | 7/1984 | Kadogaki . |
| 4,506,913 | 3/1985 | Kim ................................ 283/56 |
| 4,616,852 | 10/1986 | Cash ............................ 283/56 X |
| 4,799,712 | 1/1989 | Biava et al. . |
| 4,957,311 | 9/1990 | Geisenheimer ............ 283/48.1 |
| 4,976,351 | 12/1990 | Mangini et al. . |
| 4,991,877 | 2/1991 | Lieberman . |
| 5,004,270 | 4/1991 | Schanl et al. .............. 283/48.1 |

*Primary Examiner*—Timothy V. Eley
*Assistant Examiner*—Willmon Fridie, Jr.
*Attorney, Agent, or Firm*—Ronald S. Kosie; Robert Brouillette

[57] ABSTRACT

The present invention relates to a system whereby a consumer, and in particular a patient, may make a request that information with respect to a drug be transmitted to him or her. In accordance with the present invention, a doctor may provide a patient with an information request post card. The information request post card may, in one aspect, for example, have a first information correlation component and a second postal destination component. The first component may comprise a plurality or correlation groups, each correlation group comprising a said identification symbol and an associated check-off section for being marked so as to designate the said identification symbol, and a consumer identification section for the insertion of postal information of a consumer. The second component may have a destination information section comprising postal information of a distant site from which information about a drug associated with a designated identification symbol may be transmitted to a consumer using postal information present in said consumer identification section.

8 Claims, 3 Drawing Sheets

DOCTORS PRODUCT CODE INDEX

| | |
|---|---|
| 1. ☐ .................... | 16. ☐ |
| 2. ☐ .................... | 17. ☐ |
| 3. ☐ .................... | 18. ☐ |
| 4. ☐ .................... | 19. ☐ |
| 5. ☐ | 20. ☐ |
| 6. ☐ | 21. ☐ |
| 7. ☐ | 22. ☐ |
| 8. ☐ | 23. ☐ |
| 9. ☐ | 24. ☐ |
| 10. ☐ | 25. ☐ |
| 11. ☐ | 26. ☐ |
| 12. ☐ | 27. ☐ |
| 13. ☐ | 28. ☐ |
| 14. ☐ | 29. ☐ |
| 15. ☐ | 30. ☐ |

FIG. 1

A FREE BROCHURE HAS BEEN PREPARED FOR PATIENTS WHO TAKE THIS MEDICATION. JUST FILL IN PATIENT SECTION AND MAIL THIS CARD, AND YOU WILL RECEIVE YOUR BROCHURE BY RETURN MAIL, FREE OF CHARGE.

PRODUCT CODE INDEX

THIS SECTION FOR PHYSICIAN USE ONLY          ☑ MEDICATION

| 1. ☐  | 16. ☐ |
| 2. ☑  | 17. ☐ |
| 3. ☐  | 18. ☐ |
| 4. ☐  | 19. ☐ |
| 5. ☐  | 20. ☐ |
| 6. ☐  | 21. ☐ |
| 7. ☑  | 22. ☐ |
| 8. ☐  | 23. ☐ |
| 9. ☐  | 24. ☐ |
| 10. ☐ | 25. ☐ |
| 11. ☐ | 26. ☐ |
| 12. ☐ | 27. ☐ |
| 13. ☐ | 28. ☐ |
| 14. ☐ | 29. ☐ |
| 15. ☐ | 30. ☐ |

TO BE FILLED OUT IN
BLOCK LETTERS BY PATIENT

NAME _____
STREET _____
CITY _____
PROVINCE _____ POSTAL CODE _____
TEL. _____

BUSINESS REPLY MAIL
NO POSTAGE STAMP NECESSARY IF MAILED IN CANADA.
POSTAGE WILL BE PAID BY:

DRUG INFORMATION REQUEST SYSTEM

The present invention relates to a system whereby a consumer, and in particular a patient, may make a request that information with respect to a drug be transmitted to him or her.

It is not uncommon for a consumer to desire to have information with respect to a drug. The information may relate, for example, to possible side effects, allergic reactions, special precautions to take when using the drug, dosage guidelines, incompatibilities with other drugs, effects of alcohol and cigarette consumption during the period of use of the drug and the like. In most cases, such information is not provided with a drug. Accordingly, an interested patient receiving a (prescription) drug may request a physician or other similar type care giver to provide such information.

A physician, however, may not be fully cognisant of all of the information which the patient may request. Additionally, the relatively short time that a physician may have to provide such information may not be sufficient to allow the patient to obtain a proper understand of a physician's verbal explanations with respect to a drug; the verbal explanation(s), even if initially understood, may be too easily forgotten.

Pharmaceutical companies have been known to provide brochures which outline information such as referred to above. Proposals have been made to facilitate the distribution of such information by providing appropriate display racks, etc. immediately at a doctor's office.

U.S. Pat. No. 4,991,877, for example, teaches a drug information system which exploits a display rack for holding information cards. The difficulty with this type of in-house system is that the doctor, must undertake to insure that the documentation is available. In other words, the doctor must undertake to provide his patient(s) with access to the necessary information (e.g. documents such as brochures) in his or her office; the doctor must also undertake to ensure that the documents provided to the patient are up-to-date. This seemingly innocuous chore may, in view of the large number of drugs on the market, place an undesired burden on a physician's time, not to mention office space in order to store documents such as brochures.

Accordingly, it would be advantageous to have means wherein drug information including documentation having descriptive text of a drug, such as brochures, pamphlets, etc. and the like, need not have to be stored in a doctor's office, etc.

It would also be advantageous to have means, which facilitates the distribution of drug information, wherein a request can be made by the patient, him or herself, to obtain this information from some distant distribution center.

Accordingly, the present invention in accordance with one general aspect provides a system for providing a consumer with means for requesting drug information, said system comprising i) readable information retrieval means for presenting a plurality of index information groups, each index information group comprising a drug name and a unique identification symbol associated with said drug name, and ii) at least one information request post card having a first information correlation component and a second postal destination component, said first component comprising
a plurality of correlation groups,
each correlation group comprising a said identification symbol and an associated check-off section for being marked so as to designate the said identification symbol, and
a consumer identification section for the insertion of postal information of a consumer, said second component having a destination information section comprising postal information of a distant site from which information about a drug associated with a designated identification symbol may be transmitted to a consumer using postal information present in said consumer identification section.

A system in accordance with the present invention may, if desired, include a plurality of sample drug information documents for consultation by a disseminator of a request card, each such sample document including a descriptive text about a drug associated with an identification symbol. Such sample documents may be perused by the disseminator, such as a physician or other person, so as to familiarize him(or her)self with the information to be given to the patient so as to satisfy him(or her)self that the information is appropriate for a patient.

In accordance with the present invention, the readable information retrieval means for presenting a plurality of index information groups, may take any form, whatsoever.

The index information groups may, for example, be in machine (e.g. electronic) readable form. If so, the readable information retrieval means may, for example, comprise any (known) electronic information storage and retrieval system which may include a monitor, the required information being read from the screen thereof. The index information may, for example, be stored on a an electronically machine (e.g. computer) readable information storage medium such as a diskette, a hard disk, a tape, a compact disk or the like, the information being retrieved therefrom by using a computer having an appropriate hardware/program combination for reading the information storage medium and projecting the information on the computer's (television-like) monitor.

Alternatively, the readable information retrieval means, may take a more conventional document type form. It may, for example, comprise one or more pages of printed information; the document being consulted any time a person desires to provide a consumer with the possibility of obtaining drug information.

Thus, in accordance with a particular aspect of, the present invention there is provided a system for providing a consumer with means for requesting drug information, the system taking the form of a kit, said kit comprising i) an information document having information printed thereon, said information comprising a plurality of index information groups, each index information group comprising a drug name and a unique identification symbol associated with said drug name, said information document comprising one or more sheets or pages, and ii) at least one information request post card having a first information identification side and a second postal destination side, said first side comprising
a plurality of correlation groups, each correlation group comprising a said identification symbol and an associated check-off section for being marked so as to designate the identification symbol of said correlation group, and a consumer identification section for the insertion of postal information of a consumer, said second side having a postal information section comprising postal information of a distant site from which information about a drug associated with a designated identification symbol may be transmitted to a consumer using postal information present in said consumer identification section.

In accordance with the present invention, an identification symbol may take any form whatsoever. It may, for example, comprise a whole number. The identification symbol(s) may be used to facilitate the retrieval of information from a distant site such as a distant distribution and storage center, i.e. the symbol forming, for example, part of the storage and retrieval system of the far-away site.

In accordance with the present invention, the consumer identification section may include a group of blank spaces or zones for the insertion of the consumer's postal information, each zone being associated with some sort of indication designating the type of information to insert in the associated blank space. The postal information of the consumer may include the usual site address such as a house or apartment address of the consumer. However, if the distant site and the consumer are suitably equipped (e.g. with an operable modem equipped personal computer system), the postal information may also include a consumer's electronic mail address as may be available on commercial Bulletin Board or Database Systems. Accordingly, the drug information may be supplied to the consumer in any readable form including without limitation in printed form (e.g. in a brochure) or in electronically machine readable form (e.g. on a diskette).

A correlation group may include, in addition to the identification symbol and the associated check-off section, any other associated information or associated (blank) section(s) for the insertion of any other additional information. On the other hand, a consumer may not wish to have any indication on the request card itself which might indicate or imply to others that the consumer is taking a particular drug. Thus, a correlation group may consist of the identification symbol and the associated check-off section. Alternatively, as a compromise a correlation group may, for example, consist of the identification symbol, the associated check-off section, and, if desired, a section (i.e. blank) for the insertion of additional information such as the drug name; the blank section could be used, for example, if the consumer desires the name of the drug to be included on the request card.

As mentioned above, in accordance with the present invention, an information access system (or kit) may be provided in association with request post cards wherein the correlation groups do not include the name of the drug in association with the identification symbol. Such a system, wherein a predetermined group of identification symbols (e.g. a continuous series of whole numbers) is used for the correlation groups on the request post cards, may facilitate certain types of updating of the index information groups while avoiding the necessity to reprint request post cards to take into account any such changes; the type of updating of the index groups may, for example, include changing the whole number symbol associated with a drug or adding new a drug or drugs in association with unused identification symbols on the post card.

On the other hand it may be desired to avoid the use of an information retrieval means for presenting a plurality of index information groups by using a request postal card itself for this purpose, i.e. by including the names of the drugs directly on the request post card(s). However, each drug name, is preferably, also associated with a unique identification symbol as described above in order to facilitate the retrieval of the information at the distribution center. Thus in accordance with a further general aspect, the present invention also provides a system for providing a consumer with means for requesting drug information in the form of a kit, said kit comprising i) at least one information request post card having a first information correlation component and a second postal destination component, said first component comprising a plurality of correlation groups, each correlation group comprising of a drug name and an associated check-off section for being marked so as to designate the said drug name, and a consumer identification section for the insertion of postal information of a consumer, said second component having a destination information section comprising postal information of a distant site from which information about a drug associated with a designated identification symbol may be transmitted to a consumer using postal information present in said consumer identification section, and ii) a plurality of sample drug information documents for consultation by a disseminator of said request post cards, each said sample document including a descriptive text about a drug associated with a said identification symbol.

As mentioned above, in accordance with the present invention, drug information whether in machine readable form or in the form of printed documents may be stored at and dispensed from a distant site. This therefore will free a person such as a physician from the necessity of storing in his/her office the required documentation which can occupy needed space; and it will also free the physician from the task of reviewing the information to verify that it is current. Furthermore it is the consumer who may take on the task of inserting his/her postal information onto the provided request post card and thereafter posting or mailing it to the distant site. If the consumer has a modem/computer system (as described above) he/she may post it by E-mail (electronic mail) using any appropriate information for this purpose which may be on the request card, (provided that the distant site is equipped to provide such an electronic service).

In accordance with the present invention, the only quantity material which the doctor need store at his/her office is the information request post cards. Obviously, it will be easier for the physician to store the request cards than to store a large number of drug information documents. Since the drug information may be stored at and dispensed from a central dispensing site, this will facilitate the storage and updating of the information (e.g. printed documentation) made public by a pharmaceutical company.

The invention will now be described in relation to a particular example embodiment. It is to be understood however that the invention is in no way top be limited to the arrangements or structure as described thereto.

In the drawings which illustrate an example embodiment of the present invention;

FIG. 1 is a front view of a drug information document in accordance with the present invention;

FIG. 2 is a view of one side of an information request post card; and

FIG. 3 is a view of the other side of the information request post card illustrated in FIG. 3.

Referring to FIG. 1, an information document is shown which comprises a single (product code index) card 1. A series of whole numbers (i.e. the numbers 1 to 30) are printed on the side of the card which is shown. These numbers represent the identification symbols which may be associated with a respective drug name. In FIG. 1, by way of example, drug names are indicated generically by the dotted lines 2. Each drug name 2 is associated with a respective whole number 1 to 5; thus five index information groups are shown. The other numbers may of course each also be associated with a drug name or else be provided in reserve for the future addition of drugs to the system. The information document may include two (2) or more pages or sheets of such information cards; the index information may also be printed on both sides of the card(s).

FIG. 2 shows the information identification side of an information request post card. This side of the request post card has a correlation group section indicated generally by the reference number 3. This section is intended to be completed by the physician, etc. The correlation section includes the same identification symbols as in the product code index card of FIG. 1, i.e. in this case, namely, the whole numbers 1 to 30. Associated with each of these numbers, however, is a small check-off section 4 in the form of a blank square box; thus, thirty potential correlation groups are shown five of which in the present example would be active. Each of the correlation groups also includes a blank section 5 for the insertion of addition information as desired.

A box 4 may be marked by a physician with a check mark as shown by way, of example, near the top of the request post card. A box so marked designates the identification number associated therewith. Such a designation serves as an indication (to personnel at the distant site) that the information to be sent to the consumer is the medical information of the drug associated with the number as defined in the doctor's product code index card. The doctor may of course mark off more than one of the boxes 4; in such case, this is an indication that the information in respect of two (2) or more drugs is to be sent to the consumer. As can be seen in FIG. 2, the correlation group section does not include any reference in respect to the name of the drug for which information is to be sent to the consumer; however, this may, if desired, be added by the physician if so desired in the associated blank section 5.

With respect to the consumer, the information identification side of an information request post card has a consumer identification section or portion 6 which is provided to be filled out by the patient. The information includes the name, address, etc. of the patient to which the documents are to be sent (i.e. by mail).

Referring to FIG. 3, this figure shows the other or second side of the request information postcard. This postal destination side of the request postcard includes a postal information section or portion indicated generally by the reference numeral 7. The postal information section 7 is show as being outlined by a square area in which the predetermined postal information with respect to the distant site may be inserted. The disposition and size of the information section 7 is of course given way of an example only; the square also need not be present. The postal address could be placed more to the left or to the right as the case may be; the only criteria with respect to the information being that the correct postal information be inserted on the second destination side which would allow the postcard to be sent to and received at the distant site. Additionally, the second postal destination side will leave a portion available for the placing of a stamp or other symbol whereby the postal card could be sent via a public or national postal system (see the area indicated generally by the reference number 8). Alternatively, however, if a stamp is not used, the card could still be sent by some private means such as a private messenger system using the post information on the second side.

As mentioned above, the system may comprise a readable information retrieval means. In the above referred to disclosed example embodiment, this system takes the form of a printed information document. However, other readable information retrieval means may be used such as computers systems, etc.. The essential characteristic of the retrieval means being that the it be such that the necessary plurality of index information groups may be presented to the doctor for perusal.

As mentioned above a system in accordance with the present invention may include a plurality of sample drug information documents for consultation by a doctor, e.g. one sample document for each of the drugs listed on the product code index card. The sample information drug documents can take any form whatsoever. Their form will, however, in general, be dictated by the pharmaceutical companies who are the source of the various drugs referred to in the system; they may for example take the form of a card, brochure of two or more pages, etc.. These documents may include information and descriptive text such as is described in the U.S. Pat. No. 4,991,877 referred to above.

I claim:

1. A system for providing a consumer with means for requesting drug information, said system comprising
i) readable information retrieval means for presenting a plurality of index information groups, each index information group comprising a drug name and a unique identification symbol associated with said drug name, and
ii) at least one information request post card having a first information correlation component and a second postal destination component,
said first component comprising
a plurality of correlation groups,
each correlation group consisting of a said identification symbol and an associated check-off section for being marked so as to designate the said identification symbol, and
a consumer identification section for the insertion of postal information of a consumer,
said second component having a destination information section comprising postal information of a distant site from which information about a drug associated with a designated identification symbol may be transmitted to a consumer using postal information present in said consumer identification section.

2. A system as defined in claim 1 including a plurality of sample drug information documents for consultation by a disseminator of a said request card, each said sample document including a descriptive text about a drug associated with a said identification symbol.

3. A system as defined in claim 1 wherein each said identification symbol comprises a whole number.

4. A kit for providing a consumer with means for requesting drug information, said system comprising
i) an information document having information printed thereon, said information comprising a plurality of index information groups, each index information group comprising a drug name and a unique identification symbol associated with said drug name, said information document comprising one or more pages, and
ii) at least one information request post card having a first information identification side and a second postal destination side,
said first side comprising
a plurality of correlation groups,
each correlation group consisting of a said identification symbol and an associated check-off section for being marked so as to designate the identification symbol of said correlation group, and
a consumer identification section for the insertion of postal information of a consumer,
said second side has a postal information section comprising postal information of a distant site from which information about a drug associated with a designated identification symbol may be transmitted to a consumer using postal information present in said consumer identification section.

5. A kit as defined in claim 4 including a plurality of sample drug information documents for consultation by a disseminator of a said request card to a consumer, each said sample document including a descriptive text about a drug associated with a said identification symbol.

6. A kit as defined in claim 4 wherein each said identification symbol comprises a whole number.

7. A kit for providing a consumer with means for requesting drug information, said system comprising
i) at least one information request post card having a first information correlation component and a second postal destination component,
said first component comprising
a plurality of correlation groups,
each correlation group consisting of a said identification symbol and an associated check-off section for being marked so as to designate the said identification symbol, and
a consumer identification section for the insertion of postal information of a consumer,
said second component having a destination information section comprising postal information of a distant site from which information about a drug associated with a designated identification symbol may be transmitted to a consumer using postal information present in said consumer identification section,
and
ii) a plurality of sample drug information documents for consultation by a disseminator of said request cards, each said sample document including a descriptive text about a drug associated with a said identification symbol.

8. A kit as defined in claim 7 wherein said correlation group includes a unique identification symbol associated with said drug name.

* * * * *

UNITED STATES PATENT AND TRADEMARK OFFICE
CERTIFICATE OF CORRECTION

PATENT NO. : 5,181,743
DATED : January 26, 1993
INVENTOR(S) : Christopher Lloyd

It is certified that error appears in the above-identified patent and that said Letters Patent is hereby corrected as shown below:

At column 7, line 13 should read as follows:

requesting drug information, said kit comprising

At column 8, line 10 should read as follows:

requesting drug information, said kit comprising

Signed and Sealed this

Fourteenth Day of June, 1994

Attest:

BRUCE LEHMAN

Attesting Officer

Commissioner of Patents and Trademarks